United States Patent
Rao et al.

(10) Patent No.: US 11,873,471 B2
(45) Date of Patent: Jan. 16, 2024

(54) CULTURE DISH COMBINATION FOR EMBRYO THAWING AND EMBRYO TRANSFER

(71) Applicant: Zhejiang University, Hangzhou (CN)

(72) Inventors: Jin-peng Rao, Hangzhou (CN); Shen Tian, Hangzhou (CN); Chun Feng, Hangzhou (CN); Feng Qiu, Hangzhou (CN); Xiao-yun Wang, Hangzhou (CN); Fan Jin, Hangzhou (CN); Min Jin, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 4 days.

(21) Appl. No.: 18/105,370

(22) Filed: Feb. 3, 2023

(65) Prior Publication Data
US 2023/0357687 A1  Nov. 9, 2023

(30) Foreign Application Priority Data

May 6, 2022 (CN) .......................... 202221063907.9

(51) Int. Cl.
*C12M 1/22* (2006.01)
*C12M 1/00* (2006.01)

(52) U.S. Cl.
CPC ............ *C12M 23/10* (2013.01); *C12M 23/22* (2013.01); *C12M 23/34* (2013.01); *C12M 23/38* (2013.01)

(58) Field of Classification Search
CPC ...... C12M 23/10; C12M 23/22; C12M 23/34; C12M 23/38

(Continued)

(56) References Cited

U.S. PATENT DOCUMENTS 5,484,731 A * 1/1996 Stevens .................. C12M 23/38
220/345.5
6,156,566 A * 12/2000 Bryant ................... C12M 21/06
435/373

(Continued)

FOREIGN PATENT DOCUMENTS

JP   2004261162 A * 9/2004 ............ C12M 23/10

OTHER PUBLICATIONS

JP2004261162—A Machine English Translation (Year: 2004).*

*Primary Examiner* — Michael L Hobbs
*Assistant Examiner* — Lenora A Abel
(74) *Attorney, Agent, or Firm* — Zhigang Ma

(57) ABSTRACT

A culture dish combination for embryo thawing and embryo transfer is provided. The culture dish combination includes a first culture dish and a second culture dish, the first culture dish includes a first dish cavity for thawing and laser-assisted hatching of frozen embryos, and an opening of the first dish cavity is upward. The second culture dish is detachably connected to the first culture dish, and the second culture dish includes a second dish cavity for balancing culture medium before the embryo transfer; the second culture dish further includes a third dish cavity surrounding the second dish cavity, and openings of the second dish cavity and the third dish cavity are upward. The culture dish combination solves problems of complex operations of thawing the frozen embryo, laser-assisted hatching and the embryo transfer, which increases the accuracy of the operation of embryo thawing and improves the stability of the incubator environment.

9 Claims, 2 Drawing Sheets

(58) Field of Classification Search
USPC .................................................. 435/305.1
See application file for complete search history.

(56) References Cited

U.S. PATENT DOCUMENTS

| 7,820,433 B2* | 10/2010 | Larsen ................... C12M 23/38 |
| | | 435/287.5 |
| 2010/0075411 A1* | 3/2010 | Cecchi ................... C12M 21/06 |
| | | 435/307.1 |

* cited by examiner

CULTURE DISH COMBINATION FOR EMBRYO THAWING AND EMBRYO TRANSFER

TECHNICAL FIELD

The disclosure relates to the field of assisted reproductive technologies, in particular to a culture dish combination for embryo thawing and embryo transfer.

BACKGROUND

With the increase of age, the ovarian reserve of women tends to decline, and natural pregnancy becomes more difficult, which makes more and more women with fertility desire rely on an assisted reproductive technology, mainly in-vitro fertilization and embryo transfer (abbreviated as IVF-ET).

When IVF-ET is performed in an embryology laboratory, embryo cryopreservation is an essential procedure (including cleavage stage embryos and blastocysts cryopreservation). Frozen embryos often need to undergo a series of processes, such as thawing, laser-assisted hatching (cryopreservation leads to the hardening of the embryo's zona pellucida (ZP), thus laser thinning or drilling of ZP is performed to help the embryos hatch from ZP) and embryo transfer. Currently, the implementation of the laser-assisted hatching for thawed embryo is not often performed in Petri dishes (also referred to as culture dishes) containing a large volume of culture medium, because when the excessive volume of culture medium surrounds the embryos, the embryos are easy to drift in the culture medium, leading to difficult positioning by laser strike and even accidental injury.

In the prior art, the embryos are first placed into a microdroplet dish covered with an oil layer, and then transferred to another round dish containing a large volume of a culture medium after the laser-assisted hatching (a reason why the embryos are not ready to be transferred directly from the microdroplet dish is that the microdroplet volume is too small and the surrounding is paraffin oil for culture, so that the culture fluid and the paraffin oil could be easily sucked into the embryo transfer catheter at the same time, which increases the risk of embryo adhesion and residual in the transfer catheter). However, with the increase of the number of culture dishes, the frequency of patient's identity verification and the frequency of opening and closing the incubator also increases, which will pose challenges to the patient's identity and the stability of the incubator environment.

Therefore, the above prior art has at least following technical problems: in the prior art, operations of thawing frozen embryos, laser-assisted hatching and embryo transfer are complex. These problems are prone to errors and affect the stability of the incubator environment.

SUMMARY

By providing a culture dish combination for embryo thawing and embryo transfer, the disclosure solves technical problems in the prior art of complex operations of thawing frozen embryos, laser-assisted hatching and the embryo transfer. These technical problems are prone to errors and affect the stability of the incubator environment.

In order to solve the above technical problems, the disclosure provides the culture dish combination for embryo thawing and embryo transfer, and the culture dish combination includes:

a first culture dish, including a first dish cavity for thawing and laser-assisted hatching of frozen embryos, and an opening of the first dish cavity being upward; and a second culture dish, detachably connected to the first culture dish, where the second culture dish includes a second dish cavity for balancing culture medium before the embryo transfer and a third dish cavity surrounding the second dish cavity, and openings of the second dish cavity and the third dish cavity are upward.

In an embodiment, the first culture dish further includes a first dish bottom and a first annular wall surrounding the first dish bottom and extending upwards, and the first dish bottom is surrounded by the first annular wall to form the first dish cavity; and where the second culture dish further includes a second dish bottom, and a second annular wall is disposed on the second dish bottom, and the second dish bottom is surrounded by the second annular wall to form the second dish cavity; the periphery of the second annular wall is disposed with a third annular wall; the second dish bottom is surrounded by the third annular wall and the second annular wall to form the third dish cavity in a shape of annular, and the height of the third annular wall is higher than a height of the second annular wall.

In an embodiment, the first dish cavity, the second dish cavity and the third dish cavity are all circular cavities, and the diameter of the first dish cavity is smaller than the diameter of the third dish cavity.

In an embodiment, an outer surface of the first annular wall is provided with a convex portion.

In an embodiment, the first dish bottom is provided with recessed portions, and the recessed portions are configured to accommodate embryo culture medium droplets formed by dropwise addition.

In an embodiment, each of the recessed portions is a circular groove to facilitate forming the embryo culture medium droplets.

In an embodiment, the first dish bottom is provided with four recessed portions, three of the recessed portions are located in a first row, and the remaining one of the recessed portions is located in a second row and aligned with the recessed portion in the middle of the first row to form a T-shaped layout.

In an embodiment, the second culture dish further includes an annular stepped portion, the annular stepped portion is fixed on an inner wall of the second annular wall and protrudes towards the center of the second dish cavity, thereby forming a central dish cavity by means of enclosure of the annular stepped portion in the second dish cavity for embryo aggregation.

In an embodiment, a height of the annular stepped portion is lower than the height of the second annular wall.

In an embodiment, the first culture dish and the second culture dish are connected by a connecting piece, an end of the connecting piece is fixed with the first culture dish, the other end of the connecting piece is fixed with the second culture dish, and the connecting piece is withdrawable.

The technical solutions provided in the disclosure have the following technical advantages.

(1) Compared with the commercially available circular dishes with 35 mm and 60 mm diameters that are widely used at present, the culture dish combination in the disclosure can complete the laser-assisted hatching after thawing embryos and balancing culture medium before the embryo transfer at one time by the integrated arrangement of the first culture dish and the second culture dish. In this situation, the procedures of patients' identity information verification before transferring embryos between different dishes are simplified, the frequency of the identity verification is reduced, and repeated unpacking operations of taking dishes are decreased, which makes the embryo transfer safer and the environment of the embryo culture medium more stable. The disclosure effectively solves the technical problems in the prior art, such as the complex operations of thawing frozen embryos, laser-assisted hatching and embryo transfer. These technical problems are prone to errors and affect the stability of the incubator environment. In other words, the disclosure achieved beneficial effects of improving the accuracy of patients' identity information verification and improving the stability of the incubator environment.

(2) The periphery of the second culture dish is disposed with the third dish cavity, and the second dish cavity is surrounded by the third dish cavity. By adding a certain amount of embryo culture medium into the third dish cavity, not only could it help maintain humidity of the second dish cavity, but also it helps wash the residual oil droplets before the embryo transfer, and thus the oil could be brought into the second dish cavity as little as possible, which is conducive to the observation, and sucking and pushing of embryos during the embryo transfer.

(3) The first culture dish is detachably connected to the second culture dish, and the first culture dish is removed before placing the second culture dish containing the embryos in an incubator for the balanced culture, so as to facilitate subsequent handling and storage.

(4) The height of the third annular wall is higher than the height of the second annular wall, which effectively prevents the embryo culture medium in the third dish cavity from overflowing.

(5) By setting the recessed portions for adding the embryo culture medium droplets, the embryos can settle as far as possible in centers of the recessed portions, which makes it convenient to find the embryos under a microscope quickly and carry out laser-assisted hatching. In addition, the recessed portions also effectively reduce the height of the embryo culture medium droplets, thereby saving culture oil.

(6) Each of the recessed portion is a circular groove, and circular droplets are easier to form, thus making the process of adding the droplets more convenient.

(7) The number of the recessed portions is set to be four according to the number of thawed embryos. In most cases, embryos thawed at one time are 1 or 2 (generally, 3 or more embryos would not be thawed and transferred at one time to reduce the risk of high-order multiple pregnancy). After embryo thawing, there are still a few residues of the cryoprotectant (with certain toxicity to embryos), certain rinsing treatment must be carried out to minimize the introduction of the cryoprotectant into the embryo culture medium droplets. In this culture dish combination, the four recessed portions can provide 2-3 buffer elution areas. The circular recessed portions are arranged in a T-shaped layout with equal spacing, making it easier to determine the order of embryo culture medium droplets (better than arranged in a straight line or triangle).

(8) The outer surface of a side of the first annular wall far away from the second culture dish is provided with the convex portion. Specifically, the convex portion has a function of indicating up and down directions, which is convenient for an operator to place.

(9) The second culture dish further includes an annular stepped portion, so that the embryos can be aggregated at the central bottom of the second culture dish cavity, which is easier to find under microscope, and at the same time, the volume of the embryo culture medium in the middle area is kept in a reasonable range (the annular stepped portion can increase the height of the embryo culture medium in the middle area) to ensure stabilities of the temperature, humidity, osmotic pressure and potential of hydrogen (PH) of the embryo culture medium.

(10) The height of the second annular wall is higher than the height of the annular stepped portion, which effectively prevents the embryo culture medium in the central dish cavity from overflowing.

DETAILED DESCRIPTION OF EMBODIMENTS

Figure 1:
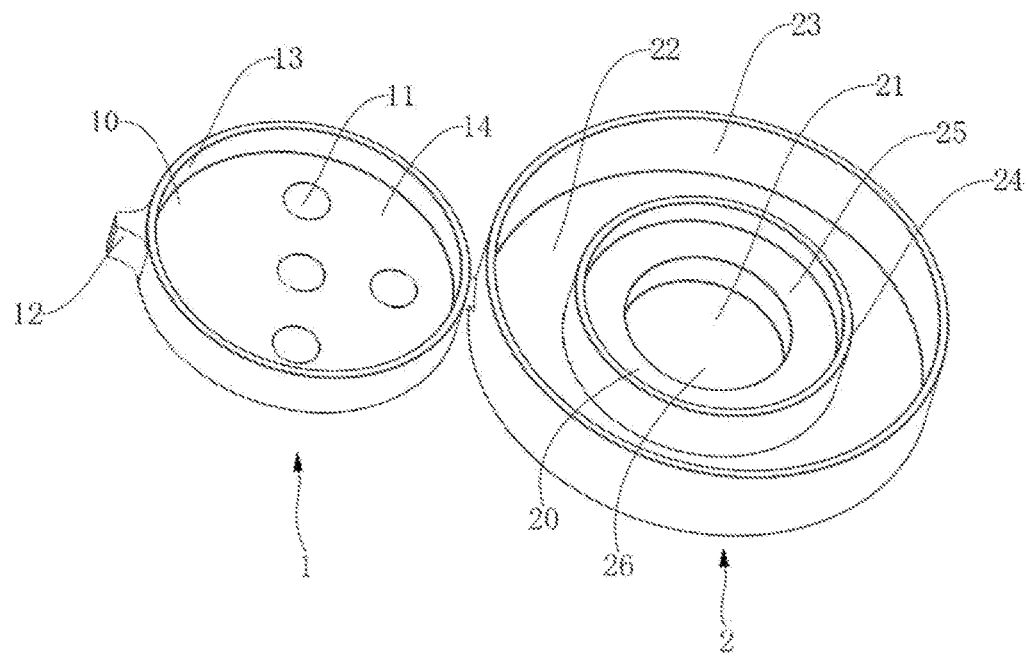
FIG. 1 is a schematic structural diagram showing a three-dimensional structure of a culture dish combination for embryo thawing and embryo transfer according to the disclosure.
Figure 2:
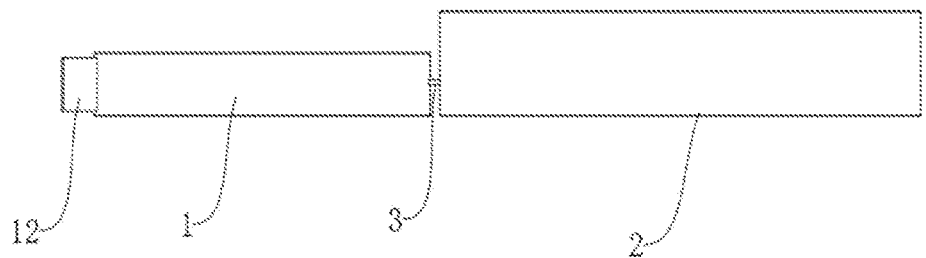
FIG. 2 is a schematic structural diagram from a side view of the culture dish combination for embryo thawing and embryo transfer according to the disclosure.

By providing a culture dish combination for embryo thawing and embryo transfer, the disclosure solves technical problems in the prior art of complex operations of thawing frozen embryos, laser-assisted hatching and embryo transfer. These technical problems are prone to errors and affect the stability of the incubator environment.

In order to solve the above technical problems, the general idea of technical solution provided by the disclosure is as follows: the laser-assisted hatching after embryos thawing and the culture medium balancing before embryo transfer can be completed at one time by the integrated arrangement of a first culture dish and a second culture dish. In this situation, the procedures of patients' identity information verification that occur when transferring embryos between different dishes are simplified, the frequency of the identity verification is reduced, and repeated unpacking operations of taking dishes are decreased, which makes the identity verification more accurate and the culture environment of embryo more stable. The disclosure effectively solves the technical problems in the prior art, including the complex operations of thawing frozen embryos, laser-assisted hatching and embryo transfer. These technical problems are prone to errors and affect the stability of the incubator environment. This culture dish combination processes the beneficial effects of facilitating the patients' identity verification and improving the stability of the incubator environment are realized.

The following is a detailed description of the technical solution of the disclosure through attached drawings and specific embodiments. It should be understood that the embodiments of the disclosure and the specific features in the embodiments are the detailed description of the technical solution of the disclosure, not a limitation to the technical solution of the disclosure. Without conflict, the embodiments of the disclosure and the technical features in the embodiments can be combined with each other.

Referring to FIGS. 1-5, the embodiments of the disclosure disclose a culture dish combination for embryo thawing and embryo transfer, the culture dish combination includes a first culture dish 1 and a second culture dish 2 that are detachably connected to each other, and the first culture dish 1 and the second culture dish 2 are horizontally connected to form a calabash shape.

The first culture dish 1 includes a first dish cavity 10 for thawing and laser-assisted hatching of frozen embryos. An opening of the first dish cavity 10 is upward to facilitate operations.

The second culture dish 2 includes a second dish cavity 20 for balancing culture medium before embryo transfer; the second culture dish 2 further includes a third dish cavity 22 which surrounds the second dish cavity 20, and openings of the second dish cavity 20 and the third dish cavity 22 are upward to facilitate operations.

Specifically, embryo culture medium droplets are dropped into recessed portions 11 of the first dish cavity 10 respectively, and then the embryo culture medium droplets are covered with paraffin oil for culture to ensure that the paraffin oil completely covers tops of the embryo culture medium droplets. A Pasteur glass tube (also referred to as a glass Pasteur pipette) is used to suck an embryo out of cryoprotectant, and the embryo is placed into the embryo culture medium droplets for rinsing to wash off the excess cryoprotectant. Then the culture dish combination is placed under an inverted microscope, and a laser is used to thin or punch the zona pellucida of the embryo to complete laser-assisted hatching. Subsequently, the Pasteur glass tube is used to suck out the embryo after the laser-assisted hatching, during the process of sucking, the Pasteur glass tube is unavoidable to pass through the paraffin oil layer. A tip of the Pasteur glass tube containing the embryo is placed into the third dish cavity 22, the paraffin oil at the tip of the Pasteur glass tube is rinsed and removed, and then the embryo is placed into the second dish cavity 20. In this situation, the first culture dish 1 is removed and discarded, and the second culture dish 2 containing the embryo is placed into an incubator for the culture medium balancing for subsequent embryo transfer.

In conclusion, compared with the commercially available circular dishes with 35 mm and 60 mm diameters that are widely used at present, the culture dish combination in the disclosure can complete the laser-assisted hatching after thawing embryos and the culture medium balancing before the embryo transfer at one time by integration arrangement of the first culture dish 1 and the second culture dish 2. In this situation, the procedures of patients' identity information verification before transferring embryos between different dishes are simplified, the frequency of the identity verification is reduced, and repeated unpacking operations of taking dishes are decreased, which makes the verification safer and the external environment of the embryo culture more stable. The disclosure effectively solves the technical problems in the prior art, such as the complex operations of thawing frozen embryos, laser-assisted hatching and embryo transfer. These technical problems are prone to errors and affect the stability of the incubator environment. The disclosure has the beneficial effects of facilitating the identity information verification of patients and maintaining the stability of the incubator environment.

In addition, the second culture dish 2 is provided with the third dish cavity 22, and the second dish cavity 20 is surrounded by the third dish cavity 22. By adding a certain amount of embryo culture medium into the third dish cavity 22, not only could it help maintain humidity in the second dish cavity 20, but also it helps wash residual oil droplets on the glass tube during the embryo transfer, and thus the oil can be brought into the second dish cavity 20 as little as possible, which is conducive to the observation and sucking and pushing of embryos during the embryo transfer.

Furthermore, the first culture dish 1 is detachably connected to the second culture dish 2, and the first culture dish 1 is removed before placing the second culture dish 2 containing the embryos in an incubator for the balanced culture, so as to facilitate subsequent handling and storage.

Figure 3:
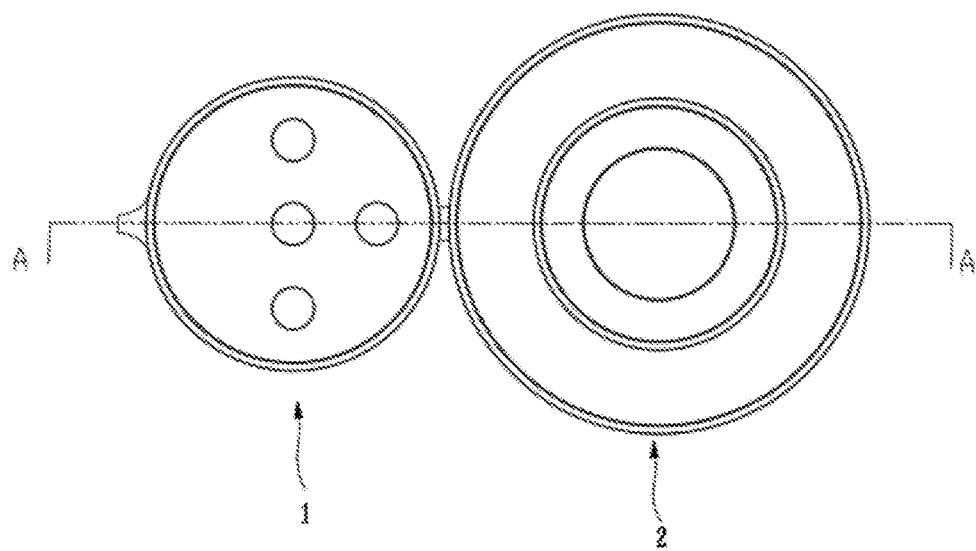
FIG. 3 is a schematic structural diagram from a top view of the culture dish combination for embryo thawing and embryo transfer according to the disclosure.
Figure 4:
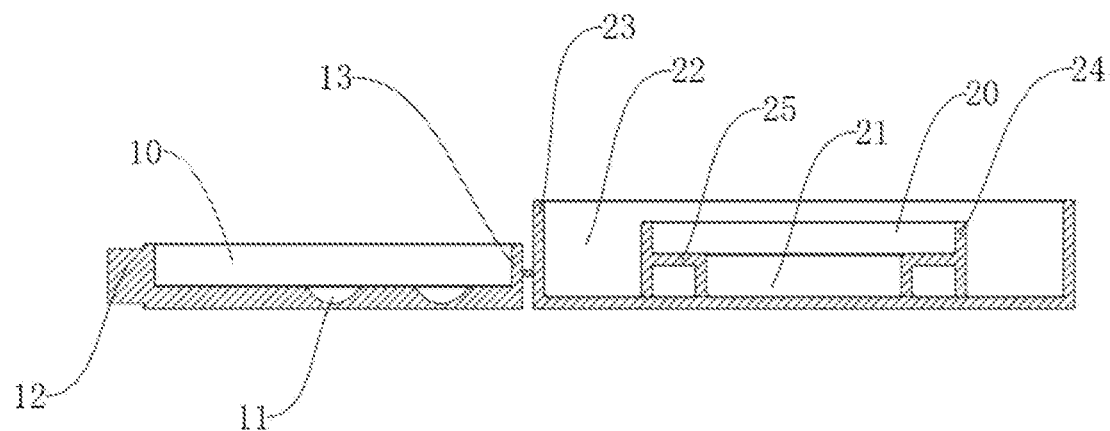
FIG. 4 is a schematic cross-sectional view of the culture dish combination for embryo thawing and embryo transfer of FIG. 3 taken along an A-A direction.
Figure 5:
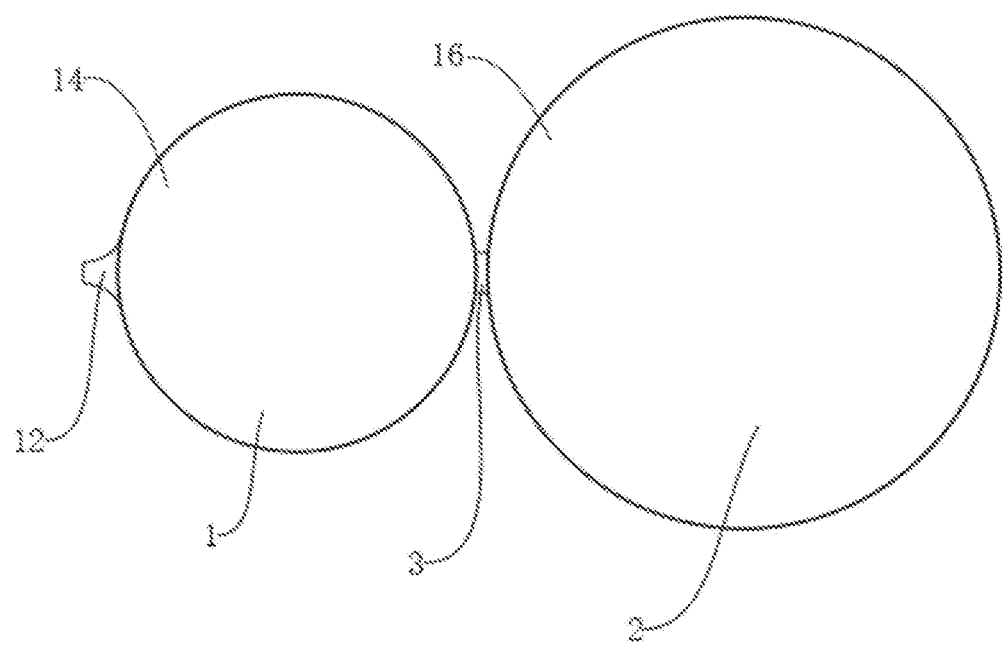
FIG. 5 is a schematic structural diagram of the culture dish combination for embryo thawing and embryo transfer from a bottom view according to the disclosure.

In some embodiments of the disclosure, as shown in FIG. 1, FIG. 3, and FIG. 4, the first culture dish 1 includes a first dish bottom 14 and a first annular wall 13 surrounding the first dish bottom 14 and extending upwards, and the first dish bottom 14 is surrounded by the first annular wall 13 to form the first dish cavity 10.

The second culture dish 2 includes a second dish bottom 26, and a second annular wall 24 is disposed on the second dish bottom 26, and the second dish bottom 26 is surrounded by the second annular wall 24 to form the second dish cavity 20. A periphery of the second annular wall 24 is disposed with a third annular wall 23; the second dish bottom 26 is surrounded by the third annular wall 23 and the second annular wall 24 to form the third dish cavity 22 in a shape of annular, and the height of the third annular wall 23 is higher than a height of the second annular wall 24.

Specifically, the first dish cavity 10, the second dish cavity 20 and the third dish cavity 22 are all circular cavities, and the diameter of the first dish cavity 10 is smaller than a diameter of the third dish cavity 22. To be specific, the diameter of the first dish cavity 10 is 35 mm, the height of the first dish cavity 10 is 6 mm, the wall thickness of the first annular wall 13 is 1 mm, and the thickness of the first dish bottom 14 is 2 mm. The diameter of the second dish cavity 20 is 30 mm, the height of the second dish cavity 20 is 7 mm, the wall thickness of the second annular wall 24 is 1 mm, and the thickness of the second dish bottom 26 is 1 mm. The diameter of the third dish cavity 22 is 50 mm, the height of the third dish cavity 22 is 10 mm, and the wall thickness of the third annular wall 23 is 1 mm. It can be understood that the height of the third annular wall 23 is higher than the height of the second annular wall 24, which is to effectively prevent the embryo culture medium in the third dish cavity 22 from overflowing.

Figure 6:
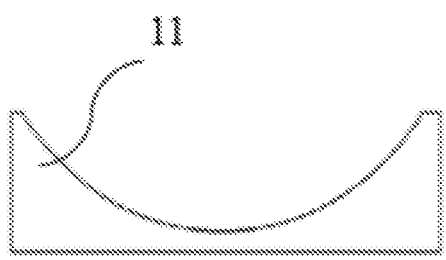
FIG. 6 is a schematic structural diagram showing a recessed portion of the culture dish combination for embryo thawing and embryo transfer according to the disclosure.

In some embodiments of the disclosure, as shown in FIG. 1, FIG. 4, and FIG. 6, some parts of the first dish bottom 14 are downward to form the recessed portions 11, and the recessed portions 11 are configured to accommodate embryo culture medium droplets formed by dropwise addition. Specifically, the embryo culture medium droplets are dropped into the recessed portions 11 of the first dish cavity 10 respectively, and then the embryo culture medium droplets are covered with paraffin oil. By setting the recessed portions 11, the embryos can be settled as far as possible in centers of the recessed portions 11, which makes it convenient to find the embryos under a microscope quickly and carry out laser-assisted hatching. In addition, the recessed portions 11 also effectively reduce the height of the embryo culture medium droplets, thereby saving the amount of culture oil (the culture oil must completely cover the embryo culture medium droplets to avoid volatilization).

In some embodiments of the disclosure, as shown in FIG. 1, FIG. 4, and FIG. 6, each of the recessed portions 11 is a circular groove, making circular droplets easier to form and adding the droplets more convenient. For example, the diameter of the recessed portion 11 is 6 mm, and the deepest depth of the recessed portion 11 is 1.6 mm. Of course, the size of the recessed portion 11 can also be other sizes suitable for use, which is not limited herein.

In some embodiments of the disclosure, as shown in FIG. 1, the first dish bottom 14 is provided with four recessed portions 11, three of the recessed portions 11 are located in a first row, and a remaining one of the recessed portions 11 is located in a second row and aligned with the recessed portion 11 in a middle of the first row to form a T-shaped layout.

Specifically, the number of the recessed portions 11 is set to four according to a number of thawed embryos. In most cases, numbers of embryo thawed at one time are 1 to 2 (generally 3 or more embryos would not thawed and transferred at one time to reduce the risk of high-order multiple pregnancy). Since there are still a few residues of the cryoprotectant around the thawed embryos, certain rinsing treatment must be carried out to minimize the introduction of the cryoprotectant (with certain toxicity to embryos) into the embryo culture medium droplets, the four recessed portions 11 can provide 2-3 buffer elution areas. The circular recessed portions are arranged in a T-shaped layout with equal spacing, it is easy to judge the order of the embryo culture medium droplets (better than arranged in a straight line or a triangle).

In some embodiments of the disclosure, as shown in FIGS. 1-4, the outer surface of a side of the first annular wall 13 far away from the second culture dish 2 is provided with a convex portion 12. Specifically, the convex portion 12 has a function of indicating up and down directions, which is convenient for an operator to place. The convex portion 12 can be in a shape of a calabash head, so as to form a complete calabash shape with the first culture dish 1 and the second culture dish 2, which makes it more ornamental and interesting. Of course, the shape of the convex portion 12 can also be other shapes, such as rectangle, circle, dot or other structures that can play an indicative role, the shape of the convex portion 12 is not limited herein.

In some embodiments of the disclosure, as shown in FIG. 1, FIG. 3, and FIG. 4, the second culture dish 2 further includes an annular stepped portion 25, the annular stepped portion 25 is fixed on an inner wall of the second annular wall 24 and protrudes towards a center of the second dish cavity, thereby forming a central dish cavity 21 through enclosure of the annular stepped portion 25 in the second dish cavity 2 for embryo aggregation.

Specifically, the annular stepped portion 25 is disposed inside the second dish cavity 20, so that the embryos can be aggregated at the central bottom of the second culture dish cavity 20, making it easier to find the embryos under the microscope, at the same time, the volume of the embryo culture medium in the central dish cavity 21 is kept in a reasonable range (the annular stepped portion 25 can increase height of the embryo culture medium in the central dish cavity 21 to ensure stabilities of the temperature, humidity, osmotic pressure and PH of the embryo culture medium. For example, the diameter of the central dish cavity 21 is 20 mm and a height of the central dish cavity 21 is 4 mm.

In some embodiments of the disclosure, as shown in FIGS. 1-4, the height of the annular stepped portion 25 is lower than the height of the second annular wall 24. Specifically, the height of the annular stepped portion 25 is 4 mm and the height of the second annular wall 24 is 7 mm. It can be understood that the height of the second annular wall 24 is higher than the height of annular stepped portion 25, which is to prevent the embryo culture medium in the central dish cavity 21 from overflowing.

In some embodiments of the disclosure, as shown in FIGS. 1-5, the first culture dish 1 and the second culture dish 2 are detachably connected by a connecting piece 3, the end of the connecting piece 3 is fixed with the first culture dish 1 by adhesion, the other end of the connecting piece 3 is fixed with the second culture dish 2 by adhesion, and the connecting piece 3 is withdrawable.

Specifically, the connecting piece 3 is a flat thin plastic sheet with a length of 6 mm, a width of 2 mm, and a thickness of 0.5 mm. The heights of connecting points of the connecting piece 3 on the first culture dish 1 and the second culture dish 2 are 3 mm from dish bottoms of the first culture dish 1 and the second culture dish 2 respectively.

The culture dish combination for embryo thawing and embryo transfer provided by the disclosure is designed as an integrated culture dish, and its working process is as follows.

(1) Preparatory Stage:

On the day before embryo thawing, embryo culture medium droplets with a volume in a range of 20 microliter (uL) to 50 uL are individually added to four circular recessed portions 11 of the first culture dish 1, and then the embryo culture medium droplets are covered with paraffin oil for culture to ensure that tops of the embryo culture medium droplets are completely covered by the paraffin oil. The embryo culture medium with a volume in a range of 600 uL to 800 uL is added into the second dish cavity of the second culture dish 2 to ensure that the height of the embryo culture medium in the second dish cavity 20 is higher than the height of an annular stepped portion 25. About 2 milliliter (mL) of the embryo culture medium is added into the third dish cavity 22 of the second culture dish 2, and the culture dish combination is placed in an incubator having saturated humidity and a carbon dioxide concentration of 6% for an overnight balancing.

(2) Embryo Thawing and Transferring Stage:

A Pasteur glass tube is used to suck an embryo out of the cryoprotectant, and the embryo is placed into four circular recessed portions 11 of the first culture dish 1 one by one, according to the sequence from front to back for rinsing to wash off the excess cryoprotectant. Then the culture dish combination is placed under an inverted microscope, with the embryo still placed in the center of one recessed portions 11, a laser is used to thin or punch the zona pellucida of the embryo to complete laser-assisted hatching. Then the Pasteur glass tube is used to suck out the embryo after the laser-assisted hatching from the recessed portion 11 of the first culture dish 1 (during the process of sucking, the Pasteur glass tube is unavoidable to pass through the paraffin oil layer). The tip of the Pasteur glass tube containing the embryo is put into the third dish cavity 22 of the second culture dish 2, where the residual paraffin oil is rinsed and removed. And then the embryo is placed into the central dish cavity 21 of the second culture dish 2, and it should be ensured that the embryo is placed into the inside of the central dish cavity 21 not on the annular stepped portion 25. In this case, the connecting piece 3 can be torn, the first culture dish 1 is removed and discarded, and the second culture dish 2 containing the embryo is put into an incubator for the balanced culture for a subsequent embryo transfer.

It should be understood that directional terms of up, down, left, right, front, rear, front side, back side, top and bottom mentioned or possibly mentioned in this specification are defined relative to the structures shown in the attached drawings. These directional terms are relative concepts, so that they could be changed according to their different positions and different use conditions. Therefore, these or other directional terms should not be interpreted as restrictive terms.

The above is only some embodiments of the disclosure and is not intended to limit the disclosure in any form or substance. It should be noted that those skilled in the art can make some improvements and supplements without departing from the method of the disclosure. These improvements and supplements should also be considered as the scope of protection of the disclosure. Without departing from the spirit and scope of the disclosure, some changes, modifications and evolutions made by those skilled in the art are equivalent embodiments of the disclosure when they use the technical contents disclosed above. In addition, any change, modification and evolution of the above embodiments based on the substantive technology of the disclosure are still within the scope of the technical solutions of the disclosure.

What is claimed is:

1. A culture dish combination for embryo thawing and embryo transfer, comprising:
    a first culture dish (1), comprising a first dish cavity (10) for thawing and laser-assisted hatching of a frozen embryo, and an opening of the first dish cavity (10) being upward; and
    a second culture dish (2), detachably connected to the first culture dish (1), wherein the second culture dish (2) comprises a second dish cavity (20) for balancing culture medium before the embryo transfer and a third dish cavity (22) surrounding the second dish cavity (20), and openings of the second dish cavity (20) and the third dish cavity (22) are upward;
    wherein the first culture dish (1) further comprises a first dish bottom (14) and a first annular wall (13) surrounding the first dish bottom (14), and the first dish bottom (14) is surrounded by the first annular wall (13) to define the first dish cavity (10); and an outer surface of the first annular wall (13) is provided with a convex portion (12) which protrudes outward along a direction perpendicular to an upward direction;
    wherein the second culture dish (2) further comprises:
        a second dish bottom (26);
        a second annular wall (24), disposed on the second dish bottom (26);
        a third annular wall (23), surrounding the second annular wall (24); and
        an annular stepped portion (25), fixed on an inner wall of the second annular wall (24) facing away from the third annular wall (23);
    wherein the annular stepped portion (25) comprises a fourth annular wall and a fifth annular wall, and the fourth annular wall is directly connected between the inner wall of the second annular wall (24) and the fifth annular wall; the third annular wall (23), the second annular wall (24) and the fifth annular wall are disposed on the second dish bottom (26) and arranged sequentially inwards from an outer edge of the second dish bottom (26), and heights of the third annular wall (23), the second annular wall (24) and the fifth annular wall gradually decrease; the second dish bottom (26) is surrounded by the second annular wall (24) to define the second dish cavity (20), the second dish bottom (26) is surrounded by the third annular wall (23) and the second annular wall (24) to define the third dish cavity (22) surrounding the second dish cavity (20) for maintaining humidity of the second dish cavity and washing residual oil droplets before the embryo transfer by adding embryo culture medium, and the second dish bottom (26) is surrounded by the fifth annular wall to define a central dish cavity (21) in the second dish cavity (20) for embryo aggregation.

2. The culture dish combination for embryo thawing and embryo transfer according to claim 1, wherein the first dish cavity (10), the second dish cavity (20) and the third dish cavity (22) are all circular cavities, and a diameter of the first dish cavity (10) is smaller than a diameter of the third dish cavity (22).

3. The culture dish combination for embryo thawing and embryo transfer according to claim 1, wherein the first dish bottom (14) is provided with recessed portions (11), and the recessed portions (11) are configured to accommodate embryo culture medium droplets formed by dropwise addition.

4. The culture dish combination for embryo thawing and embryo transfer according to claim 3, wherein each of the recessed portions (11) is a circular groove to facilitate forming the embryo culture medium droplets.

5. The culture dish combination for embryo thawing and embryo transfer according to claim 4, wherein the first dish bottom (14) is provided with four of the recessed portions (11), three of the recessed portions (11) are located in a first row, and a remaining one of the recessed portions (11) is located in a second row and aligned with the recessed portion (11) in a middle of the first row to define a T-shaped layout.

6. The culture dish combination for embryo thawing and embryo transfer according to claim 1, wherein the first culture dish (1) and the second culture dish (2) are connected by a connecting piece (3), an end of the connecting piece (3) is fixed with the first culture dish (1), the other end of the connecting piece (3) is fixed with the second culture dish (2), and the connecting piece (3) is withdrawable.

7. The culture dish combination for embryo thawing and embryo transfer according to claim 6, wherein the connecting piece (3) is a flat plastic sheet, and the first culture dish (1) is removed and discarded from the second culture dish (2) by tearing the connecting piece (3).

8. A culture dish combination for embryo thawing and embryo transfer, comprising: a first culture dish (1), a connecting piece (3), and a second culture dish (2); the connecting piece (3) is connected between the first culture dish (1) and the second culture dish (2), and the first culture dish (1) is removable from the second culture dish (2) by tearing the connecting piece (3);
    wherein the first culture dish (1) comprises a convex portion (12), a first annular wall (13), and a first dish bottom (14); the convex portion (12) is arranged on a side of the first annular wall (13) facing away from the second culture (2) and protrudes outward along a direction perpendicular to an axial direction of the first annular wall (13), and the first dish bottom (14) is surrounded by a bottom of the first annular wall (13) to define a first dish cavity (10) for thawing and laser-assisted hatching of a frozen embryo; and
    wherein the second culture dish (2) comprises a third annular wall (23), a second annular wall (24), an annular stepped portion (25), and a second dish bottom (26); the third annular wall (23), the second annular wall (24), and the annular stepped portion (25) are sequentially arranged on the second dish bottom (26) from outside to inside in that order; the second dish bottom (26) is surrounded by a bottom of the third annular wall (23) to define a third dish cavity (22) between the third annular wall (23) and the second annular wall (24) for maintaining humidity of the second dish cavity and washing residual oil droplets before the embryo transfer by adding embryo culture medium, and the second dish bottom (26) is surrounded by a bottom of the second annular wall (24) to define a second dish cavity (20) for balancing culture medium before the embryo transfer;

wherein the annular stepped portion (25) comprises a fourth annular wall and a fifth annular wall disposed on the second dish bottom (26), the fourth annular wall is directly connected between an inner wall of the second annular wall (24) facing away from the third annular wall (23) and the fifth annular wall, the second dish bottom (26) is surrounded by the fifth annular wall to define a central dish cavity (21) in the second dish cavity (20) for embryo aggregation.

9. The culture dish combination for embryo thawing and embryo transfer according to claim 8, wherein the connecting piece (3) is a flat plastic sheet which is withdrawable.

\* \* \* \* \*